(12) United States Patent  (10) Patent No.: US 6,678,090 B2
Spink  (45) Date of Patent: Jan. 13, 2004

(54) MICROSCOPE

(75) Inventor: Roger Spink, Berneck (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/949,627

(22) Filed: Sep. 12, 2001

(65) Prior Publication Data

US 2002/0126374 A1 Sep. 12, 2002

Related U.S. Application Data

(63) Continuation of application No. 08/952,463, filed as application No. PCT/EP96/02057 on May 14, 1996, now Pat. No. 6,304,372.

(30) Foreign Application Priority Data

May 17, 1995 (CH) .............................................. 1442/95

(51) Int. Cl.[7] .............................................. G02B 21/18
(52) U.S. Cl. ........................ 359/377; 359/369; 359/372
(58) Field of Search ................................ 359/368, 369, 359/372, 377, 385, 360, 363, 364

(56) References Cited

U.S. PATENT DOCUMENTS

| 3,900,144 A | | 8/1975 | Wiesler et al. ............... 359/375 |
|---|---|---|---|
| 4,166,695 A | * | 9/1979 | Hill et al. ...................... 356/28 |
| 4,443,075 A | * | 4/1984 | Crane ........................... 351/209 |
| 4,461,551 A | * | 7/1984 | Blaha ........................... 351/214 |
| 4,722,056 A | | 1/1988 | Roberts et al. ............... 600/130 |
| 4,764,005 A | | 8/1988 | Webb et al. .................. 351/205 |
| 4,902,082 A | | 2/1990 | Okabayashi et al. .......... 359/13 |
| H779 H | | 5/1990 | Verona ......................... 359/630 |
| 5,155,509 A | * | 10/1992 | Kleinberg ................... 351/205 |
| 5,355,181 A | | 10/1994 | Ashizaki et al. ............. 348/744 |
| 5,359,669 A | | 10/1994 | Shanley et al. ................ 382/2 |
| 5,369,415 A | | 11/1994 | Richard et al. ................ 345/6 |
| 5,467,104 A | | 11/1995 | Furness, III et al. ........ 359/630 |
| 5,596,339 A | | 1/1997 | Furness, III et al. ............ 348/8 |
| 5,703,637 A | | 12/1997 | Miyazaki et al. ............. 348/53 |
| 5,841,149 A | | 11/1998 | Spink et al. ........... 250/559.29 |
| 5,867,309 A | | 2/1999 | Spink et al. ................. 359/377 |
| 5,907,431 A | * | 5/1999 | Stuttler ....................... 359/379 |
| 5,953,114 A | | 9/1999 | Spink et al. .............. 356/152.1 |
| 6,043,890 A | | 3/2000 | Spink et al. ................. 356/375 |
| 6,069,733 A | | 5/2000 | Spink et al. ................. 359/388 |

FOREIGN PATENT DOCUMENTS

| CH | 00949/94-2 | 3/1994 |
|---|---|---|
| CH | 01088/94-3 | 4/1994 |
| CH | 01089/94-5 | 4/1994 |
| CH | 01090/94-1 | 4/1994 |
| CH | 01091/94-3 | 4/1994 |
| CH | 01092/94-5 | 4/1994 |
| CH | 01295/94-8 | 4/1994 |
| CH | 01525/94-0 | 5/1994 |
| CH | 03932/94-0 | 12/1994 |
| EP | 562742 A1 | 9/1993 |
| WO | 95/27226 | 10/1995 |
| WO | 95/27917 | 10/1995 |
| WO | 95/27918 | 10/1995 |
| WO | 96/20421 | 7/1996 |

* cited by examiner

*Primary Examiner*—Euncha Cherry
(74) *Attorney, Agent, or Firm*—Foley & Lardner

(57) ABSTRACT

A microscope is disclosed for observing a magnified area. Fade-in means (32a) arranged in the path (1) of the rays of the microscope (82) reflect a thin focused beam of light (101) into the path (1) of rays. The beam of light (101) is deflected or modulated by deflecting means (102) to supply an image that can be recognised by an observer (100). The image may be projected onto the object (22) either directly or indirectly, for example through a diffusing screen (108a).

20 Claims, 5 Drawing Sheets

MICROSCOPE

RELATED APPLICATIONS

This application is a continuation of patent application Ser. No. 08/952,463, filed January 9, 1998 (now U.S. Pat. No. 6,304,372), which is a 371 of International Patent Application PCT/EP96/02057, filed May 14, 1996, which claims priority from Swiss Patent Application No. 1442/95-2, filed May 17, 1995.

The invention relates to a microscope having at least one beam path and an optical system along an optical axis, and having a fade-in element for reflecting in image information for an observer's eye. Microscopes in the sense of the invention are to be understood principally, but not exclusively, as devices which have a main objective, a tube and an eyepiece for looking into. In the widest understanding of the invention, therefore, all other optically magnifying devices are to be understood which are directed onto an object to be magnified and make visible to the observer's eye a magnified image of the object observed. Microscopes, in particular stereomicroscopes, for example surgical microscopes, in particular also video (stereo) microscopes which are connected to an electronic data processing unit and/or a display are comfortable for a user when the latter is not exclusively dependent on the image currently seen through the main objective of the microscope, but also obtains when looking into the tube of the microscope additional information which is generally superimposed on the currently seen image. This can be graphic characters, symbolic representations, marks, but also superimposed images of the same object which are obtained, for example, with the aid of image processing software from the currently seen object or by means of other visualizing measures (for example X-ray pictures, CT etc.) from the same object.

Microscopes with fade-in possibilities or image superimposition possibilities are also used, inter alia, in technology, for example materials engineering, material analysis, silicon technology, criminology, etc., but also, in particular, in medicine for diagnosis, serological examinations, during operations etc.

Chiefly in the case of surgical microscopes and, in particular, during an operation, a quantity of information arises which can be of great importance to the surgeon. This is, for example, information on the patient or his state of health or patient parameters such as pulse, blood pressure, oxygen content of the blood, etc. These are in addition to the currently observed superimposing images, for example, information on specific parameters of the microscope, information on the position of the observed operation zone, as well as control data which, for example, the surgeon delivers at will via control elements such as a computer mouse or foot switch to the data processing device or to control elements for the microscope, in order to control the latter as required, for example to focus it, etc.

The use of the invention in the field of surgical microscopy will be taken up below by way of example. The invention is also applicable in other fields.

Surgical microscopes are used by the operating surgeon for optical magnification of the operation zone. Operation technology is so far advanced in this connection that magnifications in the region of 50 fold and above are no rarity. It is important during an operation that the all important information is transmitted to the operating surgeon as quickly and unambiguously as possible, in order for him to be able to conclude the operation in as short a time as possible. Since the operating surgeon preferably removes his eyes as little as possible from the eyepiece of the surgical microscope, and, conversely, difficulties of comprehension can be expected with the spoken word, it is obvious for important information such as, for example, patient data, micoscope control data or positional data to be rendered visible in the tube.

This is achieved according to known techniques by representing the relevant information on a display and reflecting the image of this display into the tube via a beam splitter. Because the user always wants a good light yield for the object observed, which can frequently be ensured by high illumination densities at the object, the problem of adequate optical density of the image reflected in or superimposed often arises in the case of reflecting in. In this case, tube displays (CRT) frequently provide no way out. The use of LCDs with strong background illuminations is attended by disadvantages in the field of resolution and also in attempting to reproduce thin lines, also since the pixel width of the LCDs is relatively large, and therefore relatively wide minimum line thicknesses are prescribed. Moreover, LCD pixels form rasters which can produce problems with edge definition and resolution.

If it is now desired, for example, to have edge improvements, image colorings, contrast improvements or other marks which are as thin as possible, and which have been prepared, for example, after prior recording by means of video technology and by means of electronic image processing, it can happen disadvantageously that the known possibilities produce unsatisfactory performance with regard to brightness and/or line thickness. Contouring would be desirable, but not achievable optimally using the means of the prior art.

A special field for the superimposition of images rises, for example, in the application of computer tomography (CT) or magnetic resonance imaging (MRI) in conjunction with stereomicroscopy. Data are obtained from CT and MRI in order to obtain a sectional image of the zone of interest from the patient which, in the final analysis after EDP, permits the representation on a computer monitor (stereo display screen) of a three-dimensional model which is faithful to reality. By using such three-dimensional images, the attending doctors are better able to localize the type and spread of the diseased area. However, it is frequently the case that both the image currently seen and the available three-dimensional representation of X-ray or CT image data are not clear enough for the relevant area to be identified during operation in a marked-off fashion with sufficient clarity from the remaining region.

As already mentioned, contour reworking or contour representation suffice for this identification to be performed optimally, but these are to be as bright and thin as possible in order not to cover other details.

Accomplishing this is one of the main objects on which the invention is based.

SUMMARY OF THE INVENTION

This object is achieved, for example, by utilizing the method and device described herein.

The problems described are eliminated by superimposing onto a first image, seen through the main objective (8) of a microscope, such as shown in FIG. 1, at least one second image from a thin, focused light beam, in particular a laser beam which is deflected and/or modulated in a deflecting device and reflected into the beam path of the microscope via a fade-in element in such a way that it visibly represents the second image for an observer's eye. A thin light beam, in particular a laser beam, can be generated in virtually arbitrarily thin and bright fashion.

It is relatively easy for the components newly required for this in accordance with the invention to be integrated into a microscope. Fade-in elements, suitable light sources, in particular lasers, are known per se to the person skilled in the art. However, despite their favorable properties, they have evidently not been used so far for the effects being sought in the field of microscopy.

It is not important here for the purpose of the invention whether the thin light beam or laser beam is projected by the optical system directly onto the retina or onto an interposed diffusing screen, or else directly in the other direction onto the object itself, in order to represent the corresponding marking there on the object surface.

Within the scope of the invention, there are both variants in which, in the operating state, the light beam extends in the region of an intermediate image plane of the optical system in a fashion approximately parallel to the optical axis in the direction of the eyepiece, and variants in which a diffusing screen on which the light beam can be scattered is arranged in the intermediate image plane.

For the purpose of the invention, a diffusing screen is in this case any optical element on which a thin light beam is scattered upon impingement in such a way that its point of contact can be seen from different points of view. Thus, this could also be an uncoated glass plate. However, it can also be, for example, a beam splitter to which a scattering coating is applied to a surface inside the optical system, or one surface of which is roughened.

According to the invention, any desired pictorial information can be fed to the observer by means of a light beam and deflecting device. In accordance with a specific embodiment of the invention, the deflecting device and/or the light source is controlled by an image processing device for contour representation, which is coupled to an image recording device which is coupled to the optical system via a further fade-in element. This permits direct feedback between the image of the object which is seen and the image represented by means of the beam. This variant is advantageous by virtue of the brightness of a focused light beam. Despite a bright operating field of view, the area to be emphasized is seen by the operating surgeon in a clearly highlighted fashion. This is so, of course, even in the case of variants in which not only the image seen optically is the basis for the image representation of the beam, but also the diagnostic data, acting as though at the same object position, from a diagnostic data device (for example a CT, MRI, PE device or the like).

In the latter variants, it is preferred to provide in each case at least one beam path per observer's eye (stereomicroscope), it being the case that in each beam path in each case one left-hand and right-hand item of partial image information, which are offset in terms of perspective in relation to the respective other one can be reflected in from one, or in each case one deflecting device via a fade-in element in each case, the deflecting device(s) being controlled by an image recognition and/or image processing device.

An image recognition device is to be understood as a system which is able to recognize the identity of the objects observed through different observation units, and in this way enables image data to be superimposed in the correct position. For this purpose, reference is made expressly to Swiss Patent Application CH3932194-0 (corresponding to WO 9620421) of the applicant, in which a particularly suitable device is described in which image data can be corrected not only for correct position but also optically and be superimposed in a fashion matched to one another. A combination of the two inventions is advantageous.

The preferred method is yielded in this connection when the deflecting device is controlled by image information obtained from the object observed through the microscope, so that, for example, contours of object details are retraced, or object details are represented by means of grid lines or the like at the actual site of the object detail in the visual field area. Of course, such grid lines have the ideal effect principally in the case of stereomicroscopes when they are used to retrace a specific object detail (for example a tumor) in three dimensions or in plastic terms.

In accordance with a development of the invention, a continuously controllable light valve is placed in front of the light source, so that a user can regulate the brightness of the image faded in by means of the beam. When conventional lamps are used, it is also possible, of course, for their brightness to be regulated via the power supply. In the case of lasers, in particular, however, the abovementioned variant is to be recommended.

Operating convenience is enhanced if the light color of the light source or of the laser can also be adjusted, something which is possible by measures known to experts in light sources or lasers.

Further advantages follow in accordance with further special embodiments of the invention in which the image observed (background image) exerts a reaction on the superimposed image. According to the invention, the procedure here is based on two points of view: relative brightness of individual pixels with respect to one another, and total brightness of the image, limited by possible adaptation behavior.

Swiss Patent Application CH1091/94-3 (corresponding to WO 9527917, WO 9527918, US 5,841,149, US 5,953,114, and US 6,043,890) describes an arrangement which permits super-impositions and data adaptations mentioned above to be enabled as quickly as possible or in real time. A combination of the present teaching with the teaching of the abovementioned application therefore provides further advantages. To this extent, the content of the abovementioned patent application is considered as being within the scope of the present disclosure.

BRIEF DESCRIPTION OF THE DRAWINGS

Further details and embodiments of the invention as well as variants thereof follow from the drawing. Of the figures represented there, by way of example.

DETAILED DESCRIPTION OF THE PREFERRED EMBODIMENTS

The figures are described together and inclusively. The same reference symbols denote identical components. The same reference symbols with different indices denote similar or functionally similar components. The invention is not restricted to the exemplary embodiments represented. Further arbitrary variants can be represented in combination chiefly with the teachings of Swiss Patent Applications CH949/94-2 (corresponding to WO 9527226, US 5,867,309, and US 6,069,733), CH1525/94-0 (corresponding to WO 9527226, US 5,867,309, and US 6,069,733), CH1295/94-8 (corresponding to WO 9527226, US 5,867,309, and US 6,069,733), CH1088/94-3 (corresponding to WO 9527917, WO 9527918, US 5,841,149, US 5,953,114, and US 6,043,890), CH1089/94-5 (corresponding to WO 9527917, WO 9527918, US 5,841,149, US 5,953,114, and US 6,043,890), CH1090/94-1 (corresponding to WO 9527917, WO 9527918, US 5,841,149, US 5,953,114, and US 6,043,890), CH1091/94-3 (corresponding to WO 9527917, WO 9527918, US 5,841,149, US 5,953,114, and US 6,043,890), CH1092/94-5 (corresponding to WO 9527917, WO 9527918, US 5,841,149, US 5,953,114, and US 6,043,890), chiefly also CH3932/94-0 (corresponding to WO 9620421). For the purpose of combining their teachings, all these applications fall under the disclosed content of this application. The attached list of reference symbols is consequently continued here.

Figure 1:
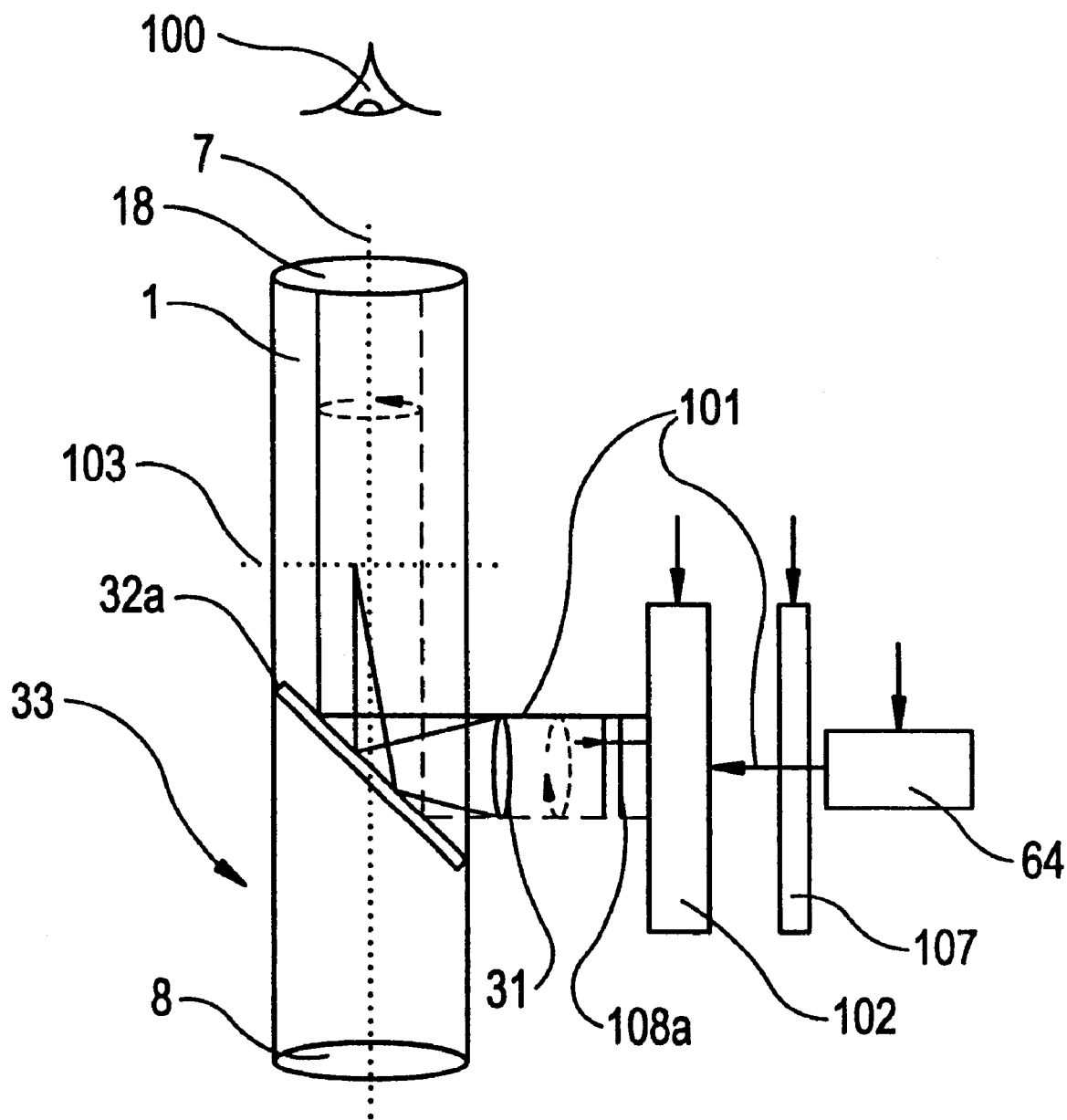
FIG. 1 shows a design principle of a microscope according to the invention, without diffusing screen.
Figure 1:
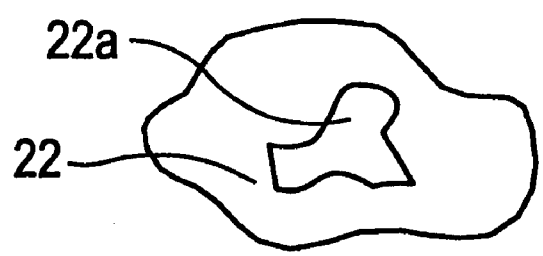

One the principles of the invention is illustrated in FIG. 1:

A beam path 1 having a magnifying optical system 33, of which only two lenses, specifically a main objective 8 and an eyepiece 18, are represented symbolically, has an obliquely positioned beam splitter 32a by means of which both the image information is directed to the eyepiece 18 through the main objective 8, and image information reflected in from the side is directed to the eyepiece 18. The beam splitter can be a semireflecting mirror or the like. It can also possibly be constructed in a miniaturized fashion as a small mirror which is bonded on a glass plate perpendicular to the optical axis 7, as is represented in Swiss Patent Application CH1092/94-5 (our ref.: R-P-3175-CH), such a latter design always functioning with divergence of the beams 101, which, if appropriate, requires additional computational outlay for the beam deflection. According to the invention, the image information reflected in from the side comprises an image of a thin, focused light beam 101, in particular a laser beam, which follows the lines to be represented pictorially in a repeated fashion at the required speed, thus rendering a coherent image, for example lines, numbers, letters, symbols, areas etc., visible to an observer. These are scattered on diffusing screen 108a and are distinguished there by a good brightness (virtually unlimited, depending on the laser power) and thus by a distinct contrast with respect to the image seen through the main objective 8. The image of the scattered laser beam is projected onto an intermediate image plane 103 of the tube by means of a lens 31 via the beam-splitting mirror 32a. The beam is deflected or moved by a deflecting device 102, known per se which has mirrors or the like which can move under control, and in this way can deflect a beam 101 irradiated into it. It goes without saying that a plurality of beams with, if appropriate, a plurality of deflecting devices as well, could also be provided simultaneously. It is also conceivable, if required, for a plurality of laser beams to be run together on the diffusing surface, in order to increase the energy density and thus the brightness. The movement of the beam 101 is represented symbolically by a dashed arrow of rotation. The beam 101 is obtained from a light source 64, in particular from a laser, which could, of course, also be integrated into the deflecting device.

Also represented in the exemplary embodiment shown is a light valve 107 which makes the brightness of the beam 101 controllable. The deflecting device 102, light valve 107 and light source 64 can preferably be controlled arbitrarily from outside, in order for the image to be represented by the beam 101 to be configured optimally in terms of beam quality for the observer, whose eye 100 is represented.

Figure 3:
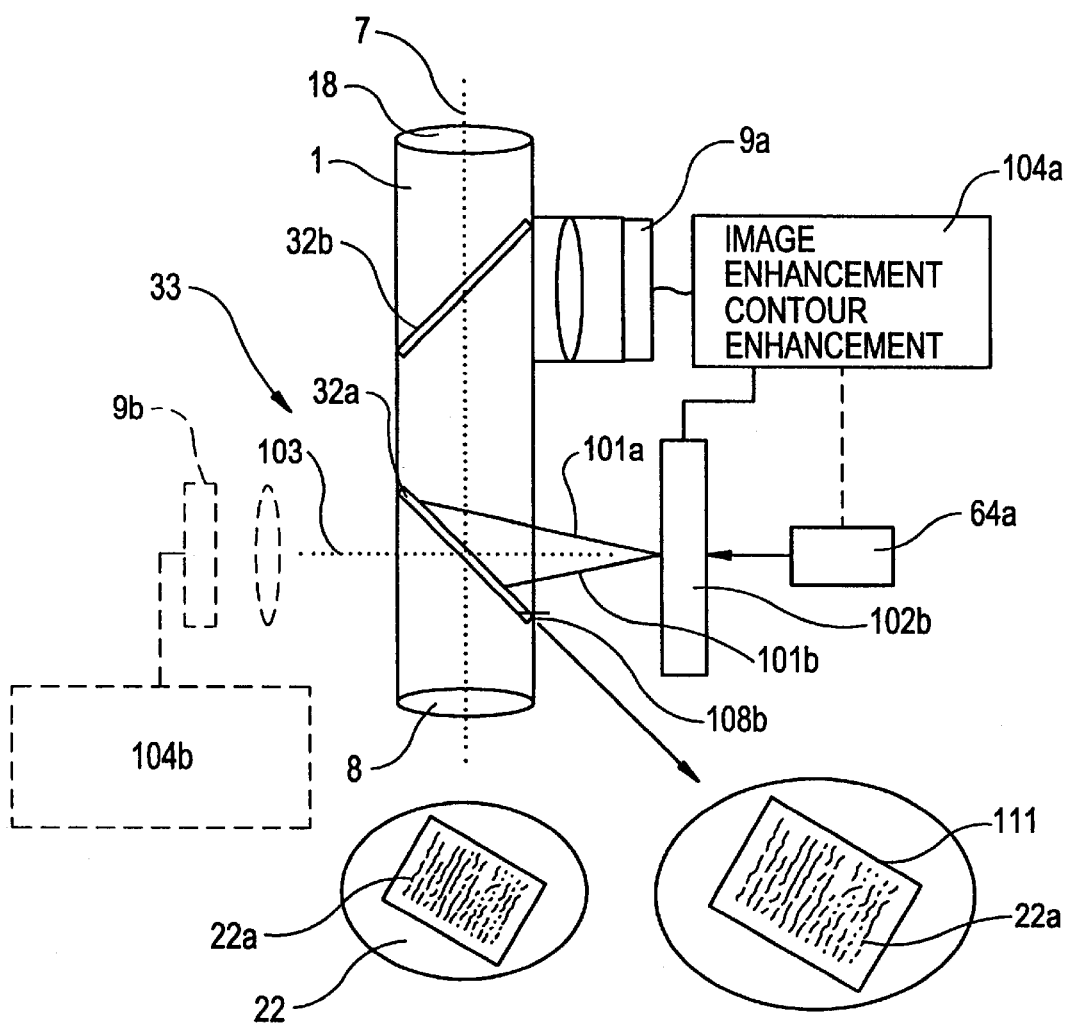
FIG. 3 shows a variant with a system for reflecting in and out additional image data and feedback therebetween.

In the exemplary embodiments in accordance with FIG. 1 and FIG. 3, the beam 101 is deflected in such a way that, via the eyepiece 18, it projects the image it produces directly into the observer's eye 100 or onto the retina thereof. The light source 64 used can thus be relatively weak optically. In the region of an intermediate image plane 103 of the optical system 33, the beams 101 are thus preferably parallel to the optical axis 7 of the optical system 33. However, it is not essential for the beam 101 to be faded in at the point shown. A variant is also conceivable in which the beam is directed into the observer's eye 100 only after the eyepiece 18. This variant is expedient particularly in combination with the teaching of Swiss Patent Application CH1092/94-5 (our ref.: R-P-3175-CH), since it does not unnecessarily increase the required distance of the eye from the eyepiece.

The object observed is represented symbolically with 22, the purpose of this design being, for example, to draw a high-contrast, bright line around an object detail 22a. The scope of the invention therefore also covers that variant in which the beam 101 is projected not directly into the observer's eye 100, but directly onto the object 22, the beam splitter 32a then having, of course, to act inversely.

Figure 2:
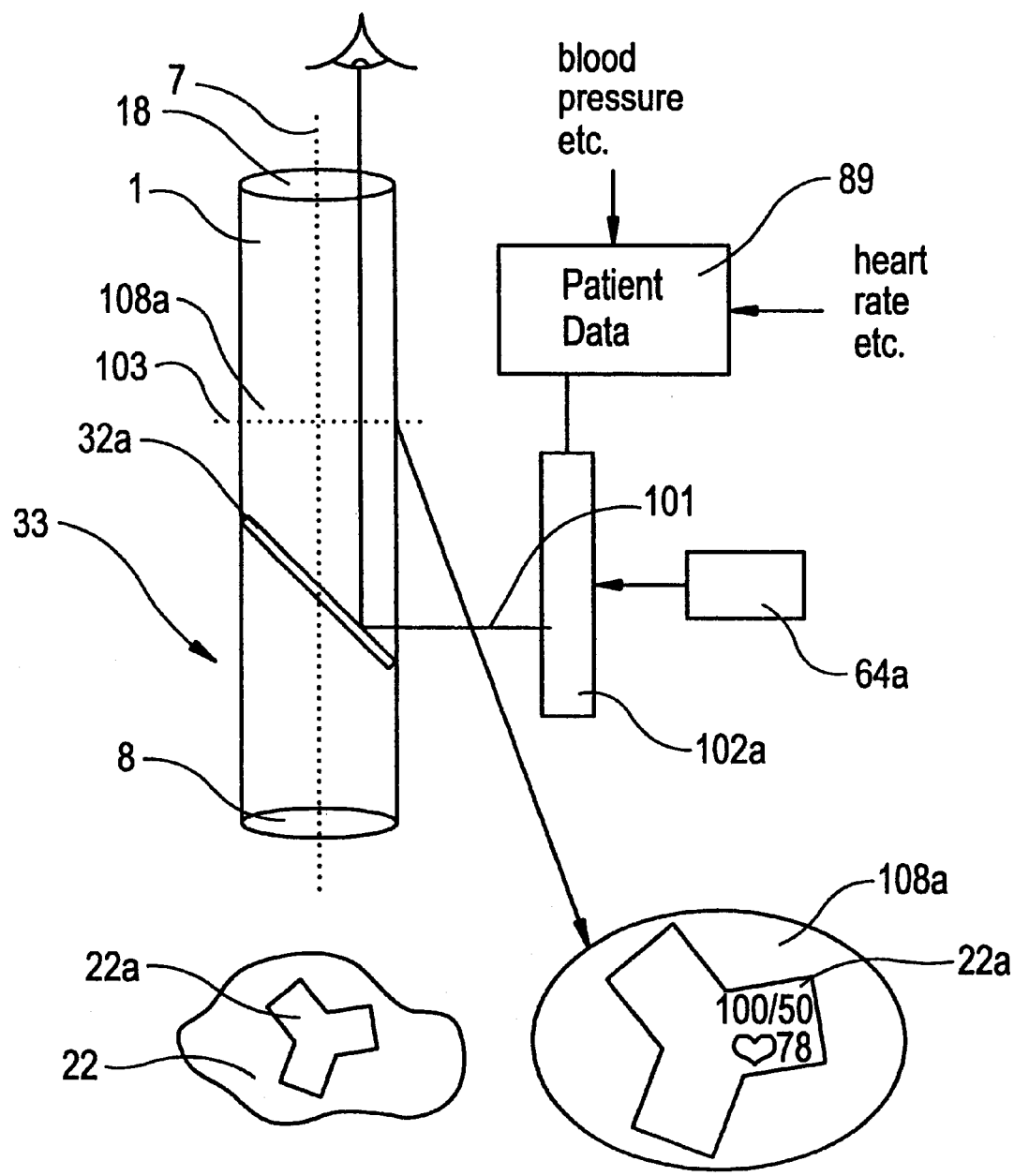
FIG. 2 shows a variant of FIG. 1 with diffusing screen and a system for reflecting in patient data.

The beam can be used to represent, for example, patient information data such as blood pressure, heart rate etc. in graphic form, as indicated in FIG. 2.

By contrast with the first variant, a laser beam 101 is directed there straight into the eye, as indicated symbolically. The optician knows the measures required to project the beam 101 correctly straight onto the retina. A diffusing screen can thereby be eliminated, and the beam can apply a high brightness and level of contrast with the correspondingly lower amount of energy. The image prescribed by the deflecting device 102a is thus produced directly on the retina and is superimposed precisely there on the image seen through the main objective 8. In this design, it is immaterial which angle the beams make with the optical axis 7, to the extent that they impinge only at the desired site on the retina. As an alternative to this design, it would be possible to use in the intermediate image plane 103 a diffusing grating at which only the wavelength region of the laser light is scattered, while the other light wavelength regions pass unimpeded, with the result that despite the diffusing screen there is no appreciable darkening of the image seen below the main objective 8.

In the example represented, blood pressure and heart rate are represented in the area of the object detail 22a which is seen. This patient information is obtained by known measuring instruments and, if appropriate, conditioned via a data conditioning unit 89 (compare Swiss Patent Application CH 1091/94-3 (our ref.: R-P-3174-CH)) in such a way that suitable control data can be fed to the deflecting device 102a in order to permit quick real-time operation.

The example represented in FIG. 3 concerns an image-processing (video) evaluation of an image seen through the main objective, for example object detail 22a through an image processing device 104a which is coupled to an image recording device 9a (for example CCD). The image recording device 9a is coupled to the beam path 1 via an imaging optical system and via a beam splitter 32b, with the result that the image processing device 104a recognizes the object detail 22a being observed. Represented by dashes are the image recording device 9b and image processing device 104b, which can be provided in addition to or as an alternative to 9a and 104a. In the variant drawn with full lines (9a, 104a), in addition to the image of the object detail 22a, the image processing device 104a also has available the image from the deflecting device 102b which is projected inversely by the device 104a. Subsequent correction is therefore easily possible. The present example is concerned with detecting contours on the object detail 22a and enhancing them by means of beam superimposition (101). This makes it easier for an operating surgeon, for example, to make out the areas involved more quickly and more clearly.

The beam splitter 32a is arranged in this example approximately centrally about an intermediate image plane 103, and is itself provided with a surface 108b which scatters to a slight extent, with the result that an additional diffusing screen is eliminated.

Figure 4:
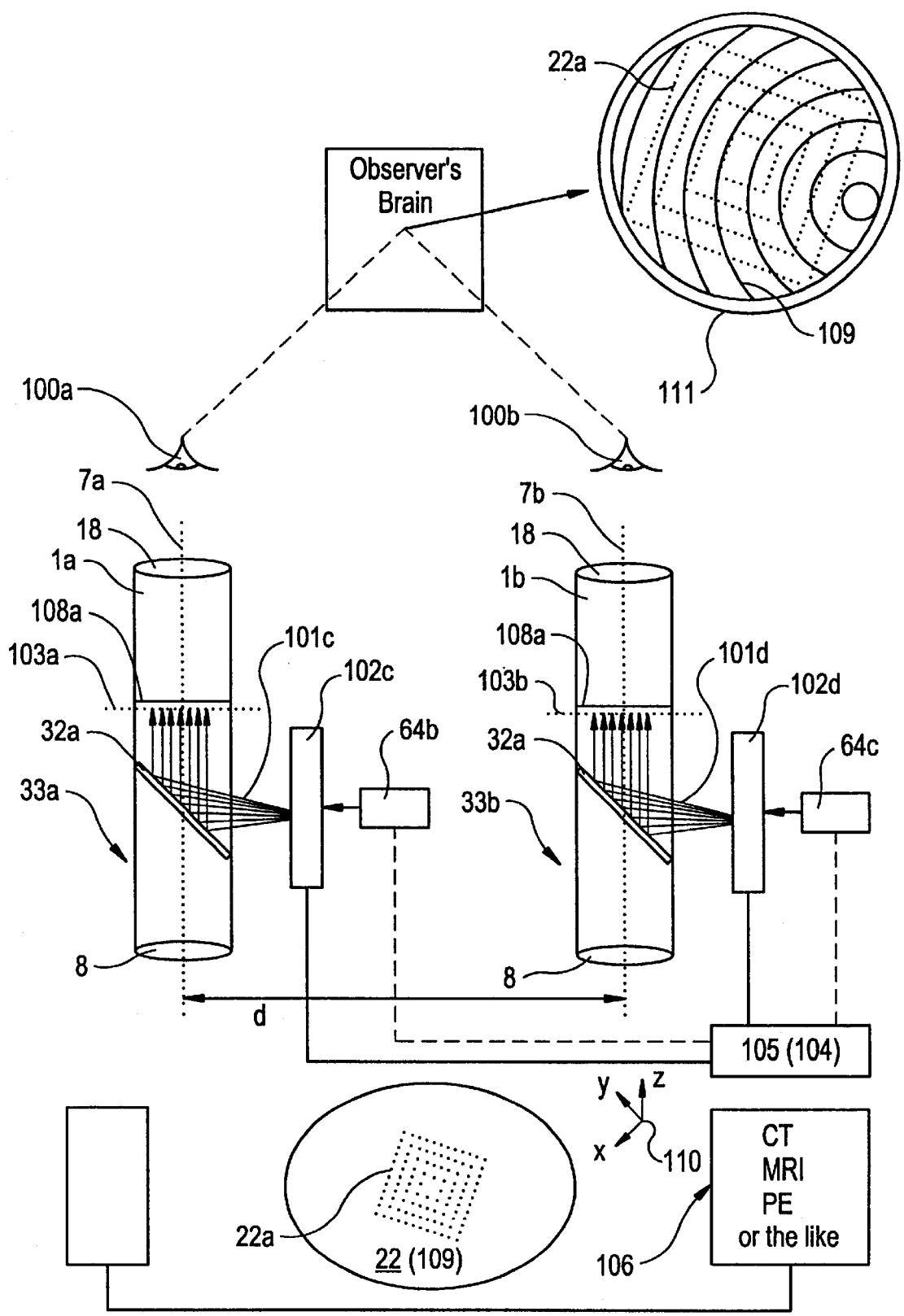
FIG. 4 shows a stereomicroscope with 3-D image super-imposition.

In the exemplary stereomicroscope in accordance with FIG. 4, diffusing screens 108a are again provided, on which partial images offset by the parallax are represented per beam path 1a, 1b relative to the respective optical axis 7a, b; said partial images are combined in the observer's brain to form a 3-D image. The deflecting devices 102c, d are driven for this purpose by an image recognition device 105, possibly with an image processing device 104, which receives its image information—possibly via a data conditioning unit (89) (not represented) and/or via an image memory—from a 3-D image data recording unit or diagnostic data device 106. The latter preferably operate not in the visible wavelength region as do the microscope beam paths, but by means of X-rays, alternating magnetic fields, positron beams, ultrasound or the like.

Thus, for example, it is possible using this design to superimpose three-dimensional grid lines calculated from the abovementioned patient data on an object detail 22a which is seen three-dimensionally or is to be seen theoretically, with the result that an operating surgeon again obtains an area of interest to him in a clear and bright fashion and highlighted with thin lines.

Of course, arbitrary combinations of superimposed images are also contained within the scope of the invention, such as alphanumeric data, contour enhancement and encirclements of areas.

Figure 5:
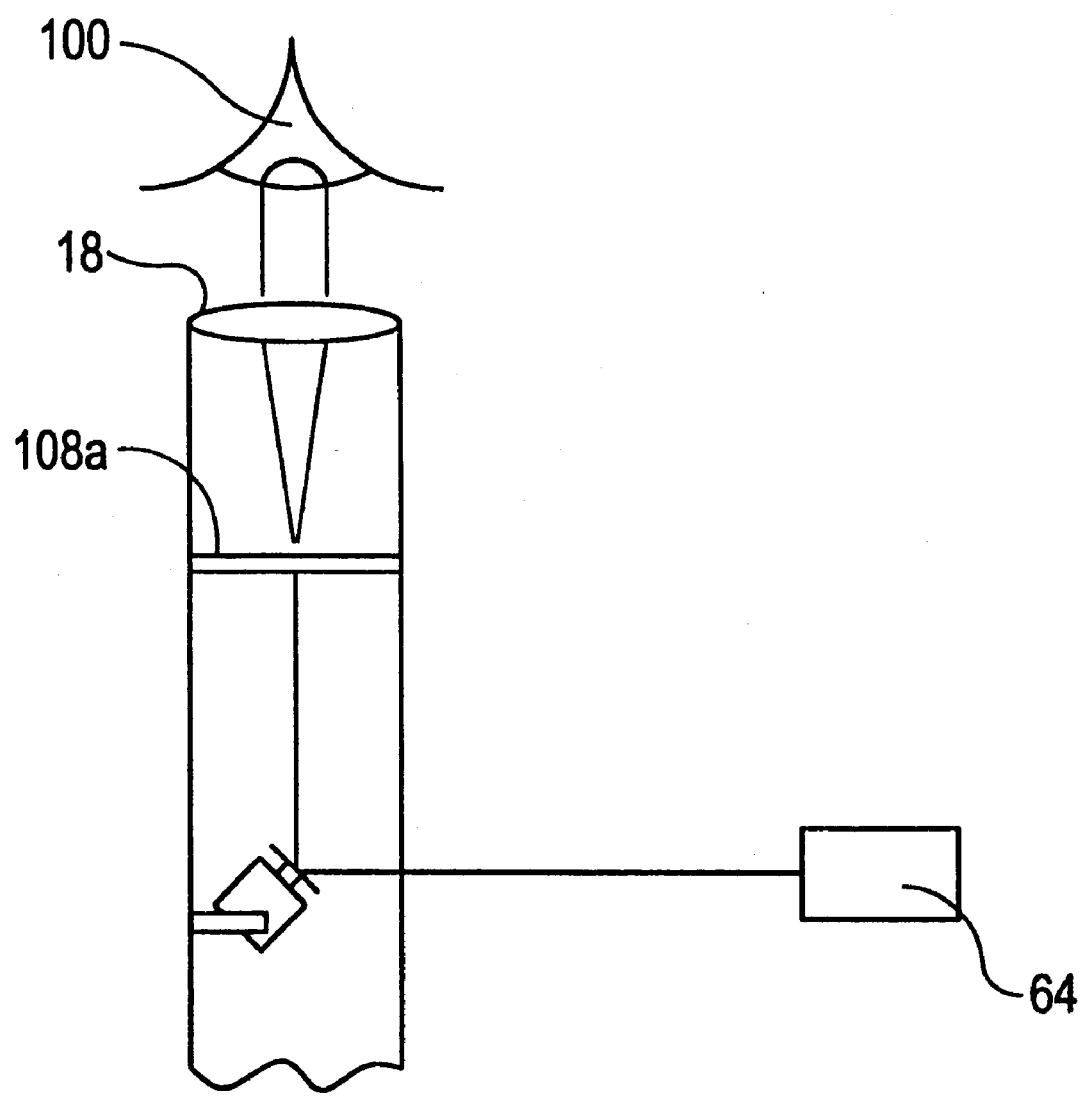
FIG. 5 shows a design with a small movable mirror in the beam path.

The variant in accordance with FIG. 5 operates with a micromirror deflecting unit having a drive in the tube 33, which directs a laser beam 101 in the correct position against the observer's eye 100.

Not shown in more detail, but familiar to the person skilled in the art as being within the scope of the invention are variants with colored lasers or with electron beams which cause suitable fluorescent screens or the like to light up with patterns. Such designs also comprise, if appropriate, vector display screens, where lines are frequently retraced in each case by the beam.

The invention also covers variants in which instead of being fed directly to the eye the light beams are firstly led to the object being observed and scattered thereon.

List of Reference Symbols

This list of reference symbols also contains reference symbols of Figures which are contained in the above-mentioned applications since, as mentioned, these count as also having been disclosed for combination purposes within the framework of this invention. This applies, in particular, to the microscopes with special beam paths and beam splitters, and to the devices for measuring the magnification and the distance from the microscope to the object as well as to microscopes for stereotactic operations etc.

1a, b First beam path
2a, b Second beam path (first beam paths laid geometrically one above another)
3 Mechano-optical switching element
   3a, 3b, 3c Opaque and preferably silvered stop
   3d LCD shutter element
   3e Micromechanical leaf mirror design
   3f LCD exchangeable shutter element
4 Beam splitters
   4a, 4b Beam splitters
   4c Beam splitter for cutting out the measuring beam
5 Screen
   5a Semicircular surface
   5b Residual surface of the screen 5
   5c Circular segment surfaces
   5d
6 Spindle for screen
7 Central axis
   7a, 7b Central axis
8 Main objective
9a Electronic image recording device
10 Display
   10a Display
11a, b Mirror
12a, b, c Adjusting device
13 Zoom
14a, b Motor
15 Reciprocal drive
16 Supply lead
17 Light source
18 Eyepiece
19 Deflecting mirror
20 Push rod
21 Rigid mirror
22 Object
   22a Object detail
23a, b, a', b', c, d Plane plate
24 Rotary actuator
25 Linkage
26
27
28
29
30 Leaf mirror of 3e
31 Tube lens
32 Fade-in element
   32a Beam splitter
   32b Mirror
   32c Second fade-in element
33 Magnifying optics
34 Arrows
35 Further mirror
36 Actuator
37 Bar
38a, b Deflecting mirrors
39 Retroprism
40 Balance weight
41 Backing plate a, b, c: prismatic with integrated mirror
42 Color filter
43 Interval switch
44 Microprocessor
45 Measuring array a
46 Reference array a
47 Module for image data transmission 48 Extraneous image data input
49 Positioning motor for zoom 13:a, b
50 Connecting lines a-g
51 Magnification display a, b, c
52 Cam disk
53 Coupling
    53a Between positioning motor 49 and zoom 13
    53b Between cam disk 52 and magnification-d [sic] display 51b
54 Mechanical tap
55a, b Pointers
56 Laser
57 Measuring beam a, b, c, c1
58 Reference beam
59 Arrows for displaceability of the fade-in element 32
60 Microscope beam path a-e
61 First deflecting element a
62 Focusing element a, b
63 Optical conductor end piece a, b
64 Light source a
65 Second deflecting element
66 Sensor
67 Distance range a
68 Connecting line
69 Distance measuring system
70 Connection
71 Magnification measuring unit
72 Position determining system a, b
73 Interferometer
74 Semireflecting mirror
75 Reflector
76 Detector
77 Electromechanical adjusting element
78 Interferometer control
79 Grating
80 Detector CCD
81 Stages
82 Microscope
83 Arrangement for measuring the magnification of the microscope
84 Arrangement for measuring the object/microscope distance
85 Position-measuring system for determining the absolute position of the microscope in space, and also for the purpose of being able to reach a conclusion upon the position of the visual field at the object from knowledge of the object/microscope distance
86 Toolbox for different user programs
87 Command control element (computer mouse)
88 Command control element for controlling the movement of the microscope (for example foot switch)
89 Data conditioning unit
90 Computer (workstation)
91 Control switch for microscope
92 Electromechanical control unit for microscope (zoom, focus, etc.)
93 Object
94 Second device (for example MRI unit or CT unit)
95 Superimposing device
96 Joint on the stand
97 Adaptive control device
98a, b Detection system
99 Memory
100a, b Observer's eye
101a, b, c Beams
102a, b, c, d Deflecting device
103a, b Intermediate image plane
104 Image processing device
105 Image recognition device
106 Diagnostic device
107 Light valve
108a, b Diffusing screen
109 Test object
110 Coordinate system
111 Enhanced contour line
112 Micromirror deflecting unit
b Spacing of the measuring beams 57a and 57b
b' Spacing of the measuring beams 57a and 57b at the measuring array
d 1, 2 Stereobasis

What is claimed is:

1. A microscope, comprising:
an ocular device to view a first image of an object,
a laser-light source for producing a thin laser beam, and
a deflecting device to deflect the thin laser beam to produce a second image to be seen by a user's eye looking into said ocular device, wherein
said deflecting device and said laser-light source are adapted to write said second image directly onto said user's eye retina.

2. The microscope according to claim 1, further comprising:
a continuously controllable light valve disposed in front of said laser-light source.

3. The microscope according to claim 1, wherein said laser-light source emits different light colors.

4. The microscope according to claim 2, wherein said laser-light source emits different light colors.

5. The microscope according to claim 2, wherein said laser-light source is controlled by an image processing device.

6. The microscope according to claim 1, wherein said laser-light source is controlled by an image processing device.

7. The microscope according to claim 1, wherein the second image is directed directly onto said user's eye retina while simultaneously displaying the first image.

8. The microscope according to claim 1, wherein the second image comprises at least one of alphanumeric data, contour enhancement, and encirclements of areas.

9. The microscope according to claim 1, wherein the second image comprises patient information of a patient being observed.

10. The microscope according to claim 1, wherein the second image is changeable on a substantially real-time basis.

11. The microscope according to claim 1, wherein the second image comprises patient information including blood pressure of a patient being observed.

12. A microscope, comprising:
a microscope eyepiece to view a first image of an object;
a laser-light source for producing a thin laser beam, and
a deflecting device to deflect the thin laser beam to produce a second image to be seen by a user's eye looking into said microscope eyepiece, wherein said deflecting device and said laser-light source are adapted to write said second image through the microscope eyepiece directly onto said user's eye retina.

13. The microscope according to claim 12, wherein said laser-light source is controlled by an image processing device.

14. The microscope according to claim 12, further comprising:

a beam splitter disposed in the microscope to direct a light beam from the laser-light source directly onto the user's retina.

15. The microscope according to claim 14, further comprising:

a microscope objective disposed between the object and the beam splitter.

16. The microscope according to claim 12, wherein the second image comprises at least one of alphanumeric data, contour enhancement, and encirclements of areas.

17. The microscope according to claim 12, wherein the second image comprises patient information of a patient being observed.

18. The microscope according to claim 12, wherein the second image is changeable on a substantially real-time basis.

19. The microscope according to claim 12, wherein the second image comprises patient information including blood pressure of a patient being observed.

20. A microscope, comprising:

a microscope eyepiece to view a first image of an object;

a laser-light source for producing a thin laser beam, and a deflecting device to deflect the thin laser beam to produce a second image to be superimposed onto the first image seen by a user's eye looking into said microscope eyepiece, wherein said deflecting device and said laser-light source are adapted to write said second image through the microscope eyepiece directly onto said user's eye retina.

* * * * *